United States Patent [19]

Staubli

[11] Patent Number: 4,579,528

[45] Date of Patent: Apr. 1, 1986

[54] DENTAL ATTACHMENT

[76] Inventor: Peter E. Staubli, 1027 Inverness Dr., San Carlos, Calif. 94070

[21] Appl. No.: 645,886

[22] Filed: Aug. 31, 1984

[51] Int. Cl.$^4$ ............................................. A61C 13/22
[52] U.S. Cl. ..................................... 433/181; 433/169
[58] Field of Search ............... 433/181, 182, 183, 180, 433/169, 170

[56] References Cited

U.S. PATENT DOCUMENTS

| | | | |
|---|---|---|---|
| 1,671,170 | 5/1928 | Takenaka | 433/182 |
| 1,688,145 | 10/1928 | Jurgensen | 433/182 |
| 1,705,504 | 3/1929 | Sorensen | 433/181 |
| 1,721,443 | 7/1929 | Gregg | 433/181 |
| 2,127,285 | 8/1938 | Brecht | 433/182 |
| 2,314,094 | 3/1943 | Lasky | 433/182 |
| 4,362,509 | 12/1982 | Sulc | 433/181 |

Primary Examiner—John J. Wilson
Attorney, Agent, or Firm—Townsend and Townsend

[57] ABSTRACT

The concept of resilient pressure fit is extended to permit ready modification according to the preference of the wearer. In particular, according to the invention, a telescopic connection mechanism includes a vertically disposed male element with a male railway which mates, in a telescopic relation, with a vertically disposed female element having a female guideway, wherein the male element is provided with an insert-receiving recess of predefined size and shape forming a transverse-oriented slot for receiving a selected variety of inserts which lock into the slot. The inserts cannot be removed from the recess slot while the male element is engaged by the female element, but the insert is readily removable from the male element when not engaged by the female element. The recess slot is bordered by wings transverse of the engagement axis of the male element and the female element.

An insert is useful for forming a lock to a latch means transverse of and in the female guideway. Various types of inserts may be used, each insert having a unique use or characteristic based on structural shape and resiliency. Each type of insert is so formed to be insertable in the slot so as to resist removal of the insert from the male element except upon the application of properly directed force transverse of the direction of the element engagement axis. Either a dental professional or the user of the appliance may remove and easily renew an insert should the insert ever wear out during the life of the appliance or should the user wish to change the fit characteristics.

2 Claims, 10 Drawing Figures

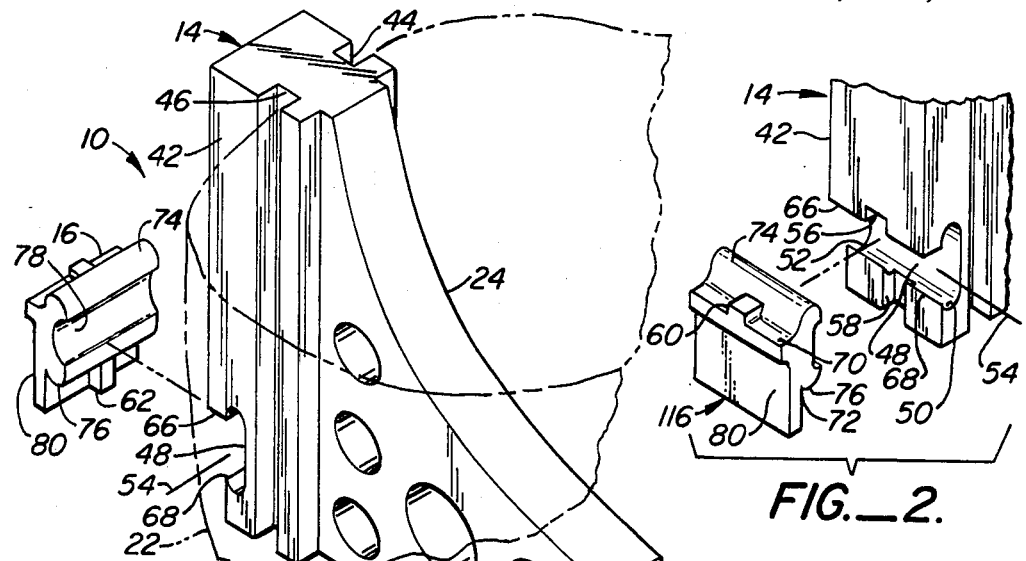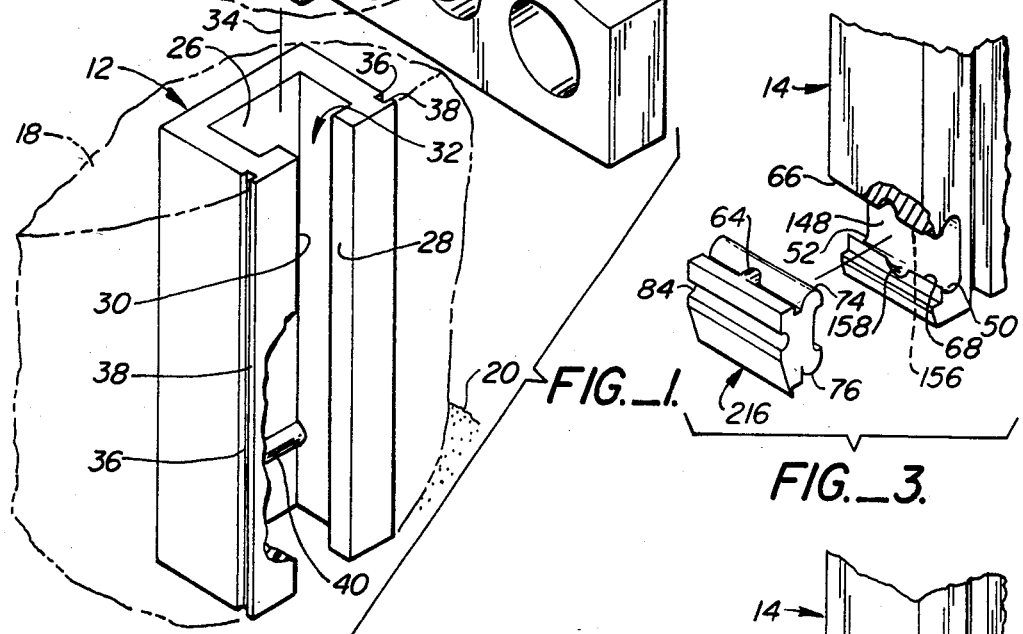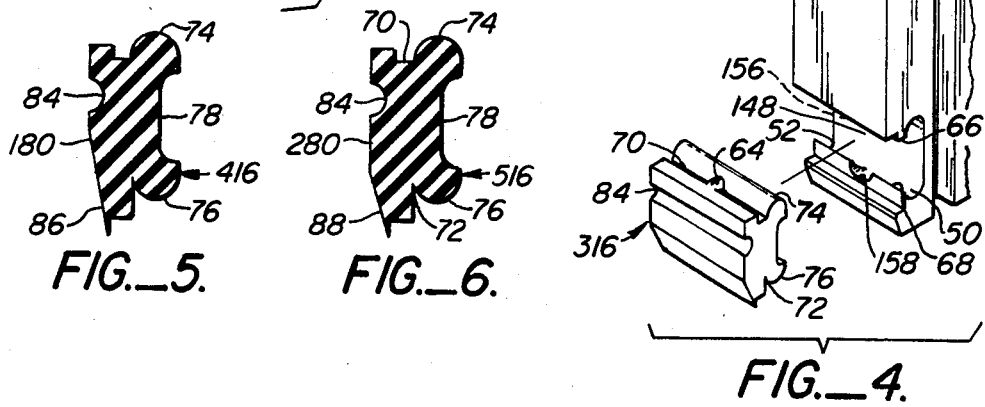

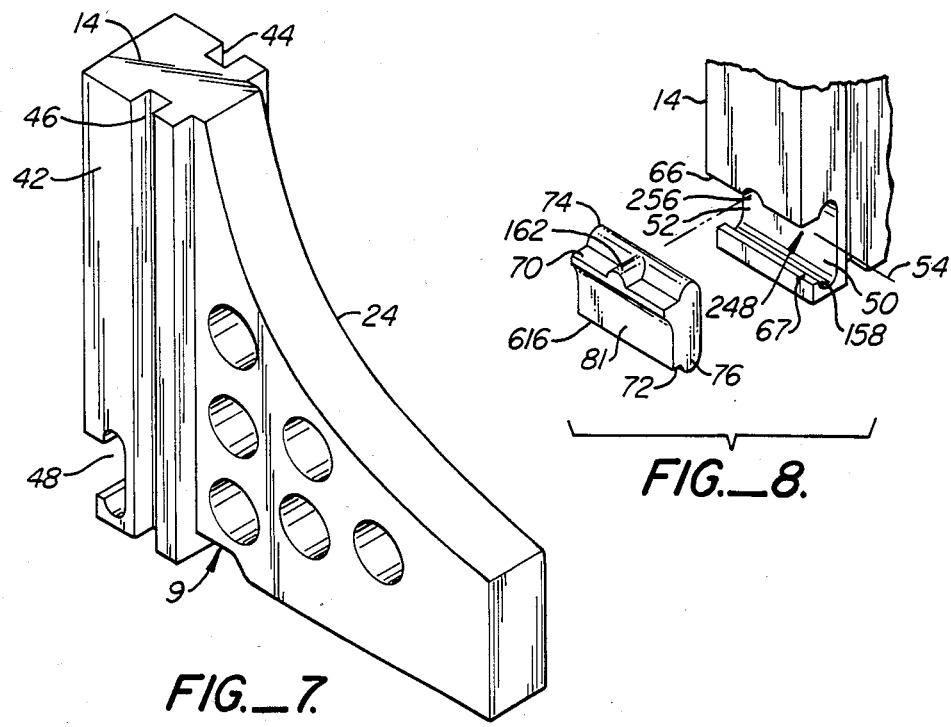
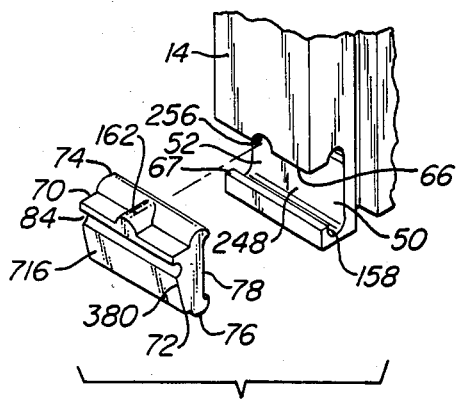
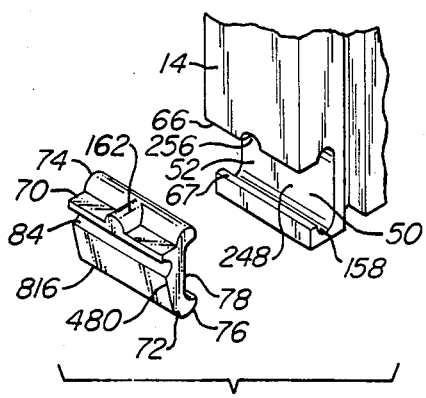

DENTAL ATTACHMENT

BACKGROUND OF THE INVENTION

This invention is related generally to apparatus for removably attaching dental structures in an oral cavity, such as bridgework or a partial denture. Dental attachment structures are characterized as comprising a male element, a female element and a connecting element.

A removable dental attachment structure presents special problems because of the necessary requirements of balance between rigidity and flexibility insuring positive stabilization without damage to soft tissue and bone structure adjacent the area to be bridged. If the attachment structure is too rigid, damage can result during normal use. If the structure is too loose, it may be dislodged inadvertently causing inconvenience and embarrassment to the wearer. One solution to the attachment problem is described in U.S. Pat. No. 4,209,904 in the name of the present inventor which describes an improvement over the Dolder bar and clip for use with a partial denture.

Telescopic attachment structures designed for easy removal present a further class of problems. Telescopic attachment structures comprise a female element with a female guideway defined along an engagement axis, a male element with a male railway which is intended to telescopically engage the female guideway along the engagement axes. Various forms of securing the female element to the male element have been developed to promote a releasable interlock between the female element and the male element. Among the developments in telescopic attachment structures have been replaceable elastomeric or like sleeves for placement between the female element and the male element and elastomeric or like coatings on the surfaces of the female element and the male element. U.S. Pat. No. 4,362,509 issued to Josef M. Sulc describes some examples of sleeves which totally separate the functional portions of the female guideway from the mail railway. This patent appears limited to structures wherein the insert completely separates the female guideway from the male railway and otherwise shields the functional portion of the male element from the functional portion of the female element.

One form of a resilient fit is found in a form of extracoronal attachment sold by APM-Sterngold of San Mateo, California under the name "Hader Vertical Extension" in which the male element and the female element are normally in direct frictional contact. The present invention represents a departure from and an advance over these types of telescopic attachment structures.

SUMMARY OF THE INVENTION

In the present invention, the concept of resilient pressure fit is extended to permit ready modification according to the preference of the wearer. In particular, according to the invention, a telescopic connection mechanism includes a vertically disposed male element with a male railway which mates, in a telescopic relation, with a vertically disposed female element having a female guideway, wherein the male element is provided with an insert-receiving recess of predefined size and shape forming a transverse-oriented slot for receiving a selected variety of inserts which lock into the slot. The inserts cannot be removed from the recess slot while the male element is engaged by the female element, but the insert is readily removable from the male element when the male element is not engaged by the female element. The recess slot is bordered by wings transverse of the engagement axis of the male element and the female element.

An insert is useful for forming a lock to a latch means transverse of and in the female guideway. Various types of inserts may be used, each insert having a unique use or characteristic based on structural shape and resiliency. Each type of insert is so formed to be insertable in the slot so as to resist removal of the insert from the male element except upon the application of properly directed force transverse of the direction of the element engagement axis. Either a dental professional or the user of the appliance may remove and easily renew an insert should the insert ever wear out during the life of the appliance or should the user wish to change the fit characteristics.

Various specific embodiments of inserts are disclosed, each with unique shape and retention characteristics. The use of each will be clear upon reference to the following detailed description in connection with the accompanying drawings.

BRIEF DESCRIPTION OF THE DRAWINGS

FIG. 1 is a perspective view in a partial denture of three primary engagement elements according to the invention.

FIG. 2 is a perspective view illustrating an insert-engagement recess slot in a male element according to the invention together with one form of an insert element according to the invention.

FIG. 3 illustrates a second form of recess slot in accordance with the invention together with a another form of insert element according to the invention.

FIG. 4 illustrates a fourth form of insert element according to the invention with the second form of recess according to the invention.

FIG. 5 is a side view of a fifth form of insert.

FIG. 6 is a side view of a sixth form of insert.

FIG. 7 is a perspective view in a partial denture of a second form of a male element with an insert-engagement recess slot.

FIG. 8 illustrates a third form of recess slot in accordance with the invention together with a seventh form of insert element according to the invention.

FIG. 9 illustrates a third form of recess slot in accordance with the invention together with a eighth form of insert element according to the invention.

FIG. 10 illustrates a third form of recess slot in accordance with the invention together with an ninth form of insert element according to the invention.

DESCRIPTION OF SPECIFIC EMBODIMENTS

In reference to FIG. 1, there is shown a perspective view of an apparatus 10 according to the invention comprising a female element 12, a male element 14 and an exemplary insert 16. The female element 12 in this particular embodiment is mounted intracoronally in a suitable gingival anchor 18 which is turn is mounted, for example, to the gingiva 20. The male element is mounted to a prosthesis 22 by means of an anchor wing 24 or the like embedded in the prosthesis 22.

The female element 12 comprises a guideway 26 having margins 28 and 30 along a longitudinal side opening 32. The side opening 32 parallels an engagement axis 34 common to the female element 12 and the male element 14. The female element 12 may be provided with recesses 36 and ridges 38 to promote secure mounting of the female element 12 to the gingival anchor 18. Further, according to one embodiment of the invention, the female element 12 is provided with a latching mechanism and, in particular, a latching ridge 40 at a predetermined location in the guideway 26 opposing the side opening 32.

The male element 14, as shown in FIGS. 1, 2, 3 and 4, comprises a railway 42 which conforms in cross section to the guideway 26. In particular, slots 44 and 46 are provided which conform to the margins 28 and 30, respectively, of the side opening 32 which are parallel to the common engagement axis 34. The slots 44 and 46 cooperate with the margins 28 and 30 to limit movement essentially to one-dimensional telescopic motion of the male element 14 in the female element 12 along the engagement axis 34. Both the male element 14 and the female element 12 are generally constructed of rigid, water-resistant material such as a metal alloy.

Each male element 14 according to the invention is provided with an insert-receiving slot 48 into which a resilient insert, such as insert 16 (FIG. 1), is removably mountable. The insert 16 occupies only a discrete segment of the railway 42 such that movement of the insert 16 along the engagement axis 34 is prohibited. Once installed, insert 16 is completely enclosed in the direction of engagement axis 34 by the male element 4, and along its outer face 80 by the female element 12. The slot 48 is provided with openings 50 and 52 opposing one another along an axis transverse of the engagement axis, that is, on opposite sides of the railway 42. In a specific embodiment, the slot 48 has a slot axis 54 which is generally parallel to a latching ridge 40 when the male element 14 is fully engaged by the female element 12. This slot axis 54 represents one direction along which an insert, such as insert 116 (FIG. 2), can be mounted to the slot 48.

There are two general types of slots but variations of these slots are possible and are within the scope of the present invention. The first type of slot, designated 48 (FIGS. 1 and 2), is provided with exposed interlocking recesses, such as interlocking recesses 56 and 58 (FIG. 2). These recesses conform with insert ridge 60 (FIG. 2) and insert ridge 62 (FIG. 1). The second type of slot, designated slot 148 (FIGS. 3 and 4), is provided with interlocking cavities 156 and 158, i.e., internal interlocking cavities, which are hidden from view when an insert, such as insert 216 or 316, is in place. The inserts 216 and 316 are provided with mating ridges 64 to interconnect with the underlying recesses.

Each slot 48 or 148 is provided with wings 66 and 68 along the margin of the slot and each type of railing insert is provided with troughs 70 and 72 for mating with the wings such that the inserts are locked against movement except along the slot axis 54 (FIG. 2). Hence, each insert is characterized by lobes 74 and 76 which abut to the opposing walls of the slot 48 or 148.

Referring to FIGS. 5 and 6, illustrating in cross-section two further types of inserts, the lobes 74 and 76 are disposed at a separation equal to or slightly greater than the corresponding dimension of a slot 148. A cavity 78 is provided between the lobes 74 and 76 thereby to provide space for the resilient material forming the insert to deform when compressed into a corresponding insert-receiving slot. As the insert 16 engaged within male element 14 is slid downwardly along engagment axis 34, insert 16 must deform along the cavity to accomodate the outward projection of transverse latch 40 before latch 40 is engaged with ridge engaging slot 84. Pressure, for example, to compress lobe 74 and lobe 76 together will force some of the resilient material into the cavity 78. Such compression will also cause the insert to bow slightly outwardly and thereby to provide a more pliant coupling with a juxtaposed wall of the female element 12. The size of the cavity 78 determines the resiliency of the insert against an opposing ridge engaging slot 84. Inserts of various shapes are therefore suggested to provide the user with a range of selections. While the shape of the cavity promotes the comfort of fit, there are other features of the insert which are noteworthy. For example, inserts, as for example insert 116 or insert 16, are provided with a flat face 80 disposed to oppose the latching ridge 40. This type of insert is used when a temporary pressure fit is intended, or more specifically, this type of insert in various sizes may be used for determining the fit of the prosthesis. It is, therefore, used only temporarily during a fitting session.

The choice of materials for inserts may be any resilient material suitable for oral placement. Nylon, polypropylene or an appropriate elastomeric material may therefore be used.

In reference to FIG. 7, there is shown a perspective view of an alternate embodiment of male element 14 wherein an optional recess 9 is located on the bottom edge of anchor wing 24. Recess 9 may be provided to lessen tissue irritation and/or inflammation.

In reference to FIG. 8, 9 and 10, there is shown a perspective view of alternative embodiments of an insert slot 248 and inserts 616, 716 and 816. The slot is provided with exposed interlocking recesses, such as interlocking recess 256. This recess conforms with insert ridge 162. The slot is provided with interlocking cavity 158 which is hidden from view when lobe 76 of an insert such as 616, 716 or 816 is in place. The slot 248 is provided with wings 66 and a surface 67 along the margin of the slot and each type of railing insert is provided with troughs 70 and 72 for mating with the wing and surface respectively such that the insert is locked against movement except along slot axis 54. Each insert is characterized by lobes 74 and 76 which abut to the opposing walls of slot 248. Further referring to FIG. 8 the insert 616 is provided with arcuate face 81 which is deposed to oppose latching ridge 40. A temporary pressure fit is intended for temporary use and is used for determining the fit of the prosthesis.

Referring to FIGS. 9 and 10 more secure fixturing may be provided where the insert 716 or 816 is provided with latching recess 84. Each latching recess conforms to the latching ridge 40 of the female element and is placed in the insert at the position where the prosthesis is to be secured relative to the latching ridge 40. The exact positioning of the recess can be modified by replacing the insert with a latching recess at a different location along the engagement axis 34. The latching recess 84 is preferably a slot transverse of the engagement axis and conforming to the shape of the latching ridge 40.

Still further, as shown in FIGS. 9 and 10 the gingival end of the insert is preferably defined by a face with a taper 380 and 480 of a preselected slope with one terminus at the recess 84 and the second terminus which will contact surface 67 when the insert is inserted into slot 248. The slope is selected to conform to the amount of retention which is desired. Referring to FIGS. 5 and 6, use of two different slopes, as shown by flat face 180 and 280 in combination with taper 86 and 88, respectively, will generally provide greater retention than use of a face with a single slope as shown by taper 380 and 480. The depth of the insert, when in place in the insert receiving slot, is sufficient to assure a frictional contact between the insert and the opposing face of the guideway in the female element. The depth or thickness, the resiliency of the insert, the size of cavity 78, if any, and all other surfaces confronting the female guideway, determine the snugness of fit between the gingival anchor 18 and the prosthesis 22. The flexibility provided by an attachment structure with removable inserts of the type herein described provides substantial flexibility not heretofore available.

The invention has now been explained with reference to specific embodiments. Other embodiments will be apparent to those of ordinary skill in the art. It is therefore not intended that this invention be limited except as indicated by the appended claims.

I claim:

1. An apparatus for attachment of a dental prosthesis to a gingival anchor, wherein said attachment include a female element and a male element, said male element for telescopically engaging said female element along a common engagement axis, said apparatus further comprising:

means forming an insert-receiving slot across a segment of said male element, said insert receiving slot defining an insert axis transverse to said engagment axis;

insert means removably mounted to said insert-receiving slot, said insert means being formed of a resilient material, said insert means generally conforming to the contour of said male element and being of a size to produce a controlled pressure fit between said female element and said male element when said female element engages said male element;

said female element further comprising a guideway having a longitudinal opening along said engagement axis and said guideway has a transverse latch means at a position to engage said insert when said male element is fully engaged by said female element;

said insert including a latch engaging means for engaging said latch and holding said male element in flexibly resilient engagement with said female element; and wherein said insert further includes means defining a cavity within a portion to be engaged by said insert-receiving slot for permitting said insert to be compressed and deformed into the space created by the cavity as said male element with said insert engaged in said insert-receiving slot is inserted along said engagement axis over said latch of said female element.

2. An apparatus for attachment of a dental prosthesis to a gingival anchor, wherein said attachment includes a female element and a male element, said male element for telescopically engaging said female element along a common engagement axis, said apparatus further comprising:

means forming an insert-receiving slot in said male element, said insert-receiving slot defining an insert axis transverse to said engagement axis, and occupying a segment spaced longitudinally apart from either end of said male element;

insert means removably mounted to said insert-receiving slot, said insert means being formed of a resilient material, said insert means being limited in the longitudinal direction by said insert-receiving slot;

latching means formed within the female element for engaging said insert;

latch engaging means formed along a face of said insert confronting said latching means in said female element; and means providing a cacity within said insert to allow deformation of a portion of said insert into the space created by said cavity such that the insert can deform as the insert passes said latching means as said male element telescopically engages said female element.

* * * * *